United States Patent
Cadwell

(10) Patent No.: US 9,730,634 B2
(45) Date of Patent: *Aug. 15, 2017

(54) APPARATUS, SYSTEM, AND METHOD FOR MAPPING THE LOCATION OF A NERVE

(71) Applicant: CADWELL LABS, Kennewick, WA (US)

(72) Inventor: John Cadwell, Kennewick, WA (US)

(73) Assignee: Cadwell Labs, Kennewick, WA (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/864,919

(22) Filed: Sep. 25, 2015

(65) Prior Publication Data

US 2016/0081621 A1 Mar. 24, 2016

Related U.S. Application Data

(63) Continuation of application No. 12/913,603, filed on Oct. 27, 2010, now Pat. No. 9,155,503.

(51) Int. Cl.
*A61B 5/00* (2006.01)
*A61B 5/0488* (2006.01)
(Continued)

(52) U.S. Cl.
CPC .......... *A61B 5/4893* (2013.01); *A61B 5/0488* (2013.01); *A61B 5/0492* (2013.01);
(Continued)

(58) Field of Classification Search
CPC .. A61B 5/04004; A61B 5/0492; A61B 5/0488
(Continued)

(56) References Cited

U.S. PATENT DOCUMENTS

| | | |
|---|---|---|
| 751,475 A | 2/1904 | De Vilbiss |
| 2,320,709 A | 6/1943 | Arnesen |

(Continued)

FOREIGN PATENT DOCUMENTS

| | | |
|---|---|---|
| EP | 0298268 | 1/1989 |
| EP | 0890341 | 1/1999 |

(Continued)

OTHER PUBLICATIONS

"Root Finding and Nonlinear Sets of Equations", Chapter 9, Numerical Recipes in C: The art of Scientific Computing, pp. 350-354 (1988-1992), htp://www.nr.com.

(Continued)

*Primary Examiner* — Michael C Stout
(74) *Attorney, Agent, or Firm* — Ropes & Gray LLP

(57) ABSTRACT

An apparatus, system, and method are disclosed for mapping the location of a nerve. The apparatus includes at least one stimulation module, a stimulation detection module, a distance module, and a mapping module. The stimulation module stimulates a nerve with an electrical stimulation current from at least one stimulation electrode. A stimulation detection module detects a muscle reaction resulting from stimulation of the nerve by the at least one stimulation electrode. The distance module uses information from the at least one stimulation electrode and from the stimulation detection module to calculate a distance between the at least one stimulation electrode and the nerve. The mapping module maps a location on the nerve using at least two distances calculated by the distance module and position information of the at least one stimulation electrode for each of the at least two distances calculated.

14 Claims, 9 Drawing Sheets

(51) Int. Cl.
*A61B 5/0492* (2006.01)
*A61B 5/055* (2006.01)
*A61B 6/00* (2006.01)
*A61B 8/08* (2006.01)
*A61B 19/00* (2006.01)
*A61N 1/08* (2006.01)

(52) U.S. Cl.
CPC ............ *A61B 5/055* (2013.01); *A61B 5/7278* (2013.01); *A61B 6/5247* (2013.01); *A61B 8/5261* (2013.01); *A61B 19/54* (2013.01); *A61N 1/08* (2013.01)

(58) Field of Classification Search
USPC ........................................ 600/546, 547, 554
See application file for complete search history.

(56) References Cited

U.S. PATENT DOCUMENTS

| | | | |
|---|---|---|---|
| 2,807,259 A | 9/1957 | Guerriero | |
| 3,682,162 A | 8/1972 | Colyer | |
| 3,985,125 A | 10/1976 | Rose | |
| 4,155,353 A | 5/1979 | Rea et al. | |
| 4,263,899 A | 4/1981 | Burgin | |
| 4,545,374 A | 10/1985 | Jacobson | |
| 4,562,832 A | 1/1986 | Wilder et al. | |
| 4,616,635 A | 10/1986 | Caspar et al. | |
| 4,705,049 A | 11/1987 | John | |
| 4,716,901 A | 1/1988 | Jackson et al. | |
| 4,765,311 A | 8/1988 | Kulik et al. | |
| 4,817,587 A | 4/1989 | Janese | |
| 4,862,891 A | 9/1989 | Smith | |
| 5,171,279 A | 12/1992 | Mathews | |
| 5,196,015 A | 3/1993 | Neubardt | |
| 5,284,153 A | 2/1994 | Raymond et al. | |
| 5,284,154 A * | 2/1994 | Raymond ................ A61B 5/05 600/554 |
| 5,299,563 A | 4/1994 | Seton | |
| 5,377,667 A | 1/1995 | Patton et al. | |
| 5,472,426 A | 12/1995 | Bonati et al. | |
| 5,474,558 A | 12/1995 | Neubardt | |
| 5,540,235 A | 7/1996 | Wilson | |
| 5,560,372 A * | 10/1996 | Cory ........................ A61B 5/05 600/547 |
| 5,565,779 A | 10/1996 | Arakawa et al. | |
| 5,601,608 A | 2/1997 | Mouchawar | |
| 5,681,265 A | 10/1997 | Maeda et al. | |
| 5,728,046 A | 3/1998 | Mayer et al. | |
| 5,741,261 A | 4/1998 | Moskovitz et al. | |
| 5,772,661 A | 6/1998 | Michelson | |
| 5,775,331 A * | 7/1998 | Raymond ................ A61N 1/05 600/554 |
| 5,785,648 A | 7/1998 | Min | |
| 5,792,044 A | 8/1998 | Foley et al. | |
| 5,795,291 A | 8/1998 | Koros et al. | |
| 5,830,150 A | 11/1998 | Palmer et al. | |
| 5,860,973 A | 1/1999 | Michelson | |
| 5,868,668 A | 2/1999 | Weiss | |
| 5,885,210 A | 3/1999 | Cox | |
| 5,891,147 A | 4/1999 | Moskovitz et al. | |
| 5,928,139 A | 7/1999 | Koros et al. | |
| 5,928,158 A | 7/1999 | Aristides | |
| 5,931,777 A | 8/1999 | Sava | |
| 5,944,658 A | 8/1999 | Koros et al. | |
| 5,954,635 A | 9/1999 | Foley et al. | |
| 5,993,385 A | 11/1999 | Johnston et al. | |
| 6,004,312 A | 12/1999 | Finneran et al. | |
| 6,004,341 A | 12/1999 | Zhu et al. | |
| 6,042,540 A | 3/2000 | Johnston et al. | |
| 6,074,343 A | 6/2000 | Nathanson et al. | |
| 6,095,987 A | 8/2000 | Shmulewitz et al. | |
| 6,139,493 A | 10/2000 | Koros et al. | |
| 6,152,871 A | 11/2000 | Foley et al. | |
| 6,181,961 B1 | 1/2001 | Prass | |
| 6,196,969 B1 | 3/2001 | Bester et al. | |
| 6,206,826 B1 | 3/2001 | Mathews et al. | |
| 6,224,545 B1 | 5/2001 | Cocchia et al. | |
| 6,259,945 B1 | 7/2001 | Epstein et al. | |
| 6,266,558 B1 | 7/2001 | Gozani et al. | |
| 6,287,322 B1 | 9/2001 | Zhu et al. | |
| 6,302,842 B1 | 10/2001 | Auerbach et al. | |
| 6,306,100 B1 | 10/2001 | Prass | |
| 6,309,349 B1 | 10/2001 | Bertolero et al. | |
| 6,325,764 B1 | 12/2001 | Griffith et al. | |
| 6,334,068 B1 | 12/2001 | Hacker | |
| 6,425,859 B1 | 7/2002 | Foley et al. | |
| 6,450,952 B1 | 9/2002 | Rioux et al. | |
| 6,466,817 B1 | 10/2002 | Kaula et al. | |
| 6,500,128 B2 | 12/2002 | Marino | |
| 6,535,759 B1 | 3/2003 | Epstein et al. | |
| 6,609,018 B2 | 8/2003 | Cory et al. | |
| 6,712,795 B1 | 3/2004 | Cohen | |
| 6,847,849 B2 | 1/2005 | Mamo et al. | |
| 6,851,430 B2 | 2/2005 | Tsou | |
| 6,926,728 B2 | 8/2005 | Zucherman et al. | |
| 6,945,933 B2 | 9/2005 | Branch et al. | |
| 7,089,059 B1 | 8/2006 | Pless | |
| 7,104,965 B1 | 9/2006 | Jiang et al. | |
| 7,177,677 B2 | 2/2007 | Kaula et al. | |
| 7,214,197 B2 | 5/2007 | Prass | |
| 7,261,688 B2 | 8/2007 | Smith et al. | |
| 7,470,236 B1 | 12/2008 | Kelleher et al. | |
| 7,522,953 B2 | 4/2009 | Kaula et al. | |
| 7,713,210 B2 | 5/2010 | Byrd et al. | |
| 7,983,761 B2 * | 7/2011 | Giuntoli ............ A61B 5/04001 600/554 |
| 8,147,421 B2 | 4/2012 | Farquhar et al. | |
| 8,160,694 B2 | 4/2012 | Salmon et al. | |
| 8,192,437 B2 | 6/2012 | Simonson | |
| 2002/0007188 A1 * | 1/2002 | Arambula .......... A61B 17/1757 606/130 |
| 2002/0095080 A1 * | 7/2002 | Cory ................ A61B 5/04001 600/393 |
| 2003/0045808 A1 | 3/2003 | Kaula et al. | |
| 2005/0075578 A1 * | 4/2005 | Gharib ................ A61B 5/0492 600/546 |
| 2005/0182454 A1 * | 8/2005 | Gharib ................ A61B 5/0488 607/48 |
| 2006/0009754 A1 * | 1/2006 | Boese ................ A61B 18/1492 606/29 |
| 2006/0085048 A1 * | 4/2006 | Cory .................... A61B 5/0536 607/48 |
| 2006/0085049 A1 * | 4/2006 | Cory .................... A61B 5/0536 607/48 |
| 2006/0122514 A1 * | 6/2006 | Byrd ........................ A61B 5/06 600/466 |
| 2006/0258951 A1 | 11/2006 | Bleich et al. | |
| 2007/0016097 A1 * | 1/2007 | Farquhar .............. A61B 5/0488 600/546 |
| 2007/0021682 A1 * | 1/2007 | Gharib ................ A61B 5/0488 600/546 |
| 2007/0032841 A1 * | 2/2007 | Urmey .............. A61N 1/36021 607/72 |
| 2007/0049962 A1 | 3/2007 | Marino et al. | |
| 2007/0184422 A1 * | 8/2007 | Takahashi ........................ 607/72 |
| 2008/0027507 A1 * | 1/2008 | Bijelic ................ G06F 19/3437 434/262 |
| 2008/0058606 A1 | 3/2008 | Miles et al. | |
| 2008/0065144 A1 | 3/2008 | Marino et al. | |
| 2008/0071191 A1 | 3/2008 | Kelleher et al. | |
| 2008/0082136 A1 * | 4/2008 | Gaudiani ............ A61N 1/0452 607/48 |
| 2008/0097164 A1 | 4/2008 | Miles et al. | |
| 2008/0167574 A1 | 7/2008 | Farquhar | |
| 2008/0194970 A1 | 8/2008 | Steers et al. | |
| 2008/0269777 A1 * | 10/2008 | Appenrodt ......... A61B 17/3468 607/9 |
| 2008/0281313 A1 | 11/2008 | Fagin et al. | |
| 2009/0018399 A1 | 1/2009 | Martinelli et al. | |
| 2009/0088660 A1 * | 4/2009 | McMorrow .......... A61B 5/4041 600/546 |

(56) References Cited

U.S. PATENT DOCUMENTS

| | | | |
|---|---|---|---|
| 2009/0105604 A1* | 4/2009 | Bertagnoli | A61B 19/201 606/130 |
| 2009/0177112 A1 | 7/2009 | Gharib et al. | |
| 2009/0204016 A1 | 8/2009 | Gharib et al. | |
| 2009/0209879 A1 | 8/2009 | Kaula et al. | |
| 2009/0259108 A1* | 10/2009 | Miles | A61B 5/0059 600/546 |
| 2009/0279767 A1* | 11/2009 | Kukuk | A61B 5/0492 600/202 |
| 2010/0036384 A1* | 2/2010 | Gorek | G06T 7/0044 382/132 |
| 2010/0106011 A1 | 4/2010 | Byrd et al. | |
| 2010/0152604 A1 | 6/2010 | Kaula et al. | |
| 2010/0286554 A1* | 11/2010 | Davis | A61B 19/5244 606/104 |
| 2010/0317989 A1 | 12/2010 | Gharib et al. | |
| 2011/0082383 A1 | 4/2011 | Cory et al. | |
| 2011/0184308 A1 | 7/2011 | Kaula et al. | |
| 2011/0295579 A1* | 12/2011 | Tang | A61N 1/0408 600/554 |
| 2011/0313530 A1 | 12/2011 | Gharib et al. | |
| 2012/0109000 A1 | 5/2012 | Kaula et al. | |
| 2012/0220891 A1 | 8/2012 | Kaula et al. | |
| 2012/0238893 A1 | 9/2012 | Farquhar et al. | |
| 2012/0296230 A1 | 11/2012 | Davis et al. | |

FOREIGN PATENT DOCUMENTS

| | | |
|---|---|---|
| EP | 0972538 | 1/2000 |
| WO | WO-00/38574 | 7/2000 |
| WO | WO-00/66217 | 11/2000 |
| WO | WO-01/37728 | 5/2001 |
| WO | WO-03/005887 | 1/2003 |
| WO | WO-2005/030318 | 4/2005 |
| WO | WO-2006/042241 | 4/2006 |

OTHER PUBLICATIONS

Bergey, et al., "Endoscopic Lateral TransPsoas Approach to the Lumbar Spine", Spine, 29(15):1681-1688 (2004).

Bertagnoli, et al., "The AnteroLateral transPsoatic Approach (ALPA), A New Technique for Implanting Prosthetic Disc-Nucleus Devices", Journal of Spinal Disorders and Techniques, 16(4):398-404 (2003).

Bose, et al., "Neurophysiologic Monitoring of Spinal Nerve Root Function During Instrumented Posterior Lumbar Spine Surgery", Spine, 27(13):1440-1450 (2002).

Butterworth, et al., "Effects of Halothane and Enflurane on Firing Threshold of Frog Myelinated Axons", Journal of Physiology, 411:493-516 (1989).

Calancie, et al., Stimulus-Evoked EMG Monitoring During Transpedicular Lumbosacral Spine Instrumentation, Initial Clinical Results, Spine, 19(24):2780-2786 (1994).

Calancie, et al., "Threshold-level multipulse transcranial electrical stimulation of motor cortex for intraoperative monitoring of spinal motor tracts: description of method and comparison to somatosensory evoked potential monitoring", Journal of Neurosurgery, 88:457-470 (1998).

Calancie, et al., "Threshold-level repetitive transcranial electrical stimulation for intraoperative monitoring of central motor conduction", Journal of Neurosurgery, 95:161-168 (2001).

Clements, et al., "Evoked and Spontaneous Electromyography to Evaluate Lumbosacral Pedicle Screw Placement", Spine, 21(5):600-604 (1996).

Danesh-Clough, et al., "The Use of Evoked EMG in Detecting Misplaced Thoracolumbar Pedicle Screws", Spine, 26(12):1313-1316 (2001).

Deletis, et al., "The Role of Intraoperative Neurophysiology in the Protection or Documentation of Surgically Induced Injury to the Spinal Cord", Annals of the New York Academy of Sciences, 939:137-144 (2001).

Dezawa, et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", 3(4):301-307 (1997).

Digitimer Ltd., 37 Hydeway, Welwyn Garden City, Hertfordshire. AL7 3BE England, email. sales@digitimer.com, website: www.digitimer.com, "Constant Current High Voltage Stimulator, Model DS7A, for Percutaneous Stimulation of Nerve and Muscle Tissue" (1988).

Epstein, et al., "Evaluation of Intraoperative Somatosensory-Evoked Potential Monitoring During 100 Cervical Operations", Spine, 18(6):737-747 (1993).

Foley, et al., "Microendoscipic Discectomy", Techniques in Neurosurgery, 3:(4):301-307 (1997).

Ford, et al., "Electrical Characteristics of Peripheral Nerve Stimulators, Implications for Nerve Localization", Dept. of Anesthesia, University of Cincinnati College of Medicine, Cincinnati, OH 45267, pp. 73-77.

Gardocki, "Tubular diskectomy minimizes collateral damage", AAOS Now, Sep. 2009 Issue, http://www.aaos.org/news/aaosnow/sep09/clinical12.asp.

Glassman, et al., "A Prospective Analysis of Intraoperative Electromyographic Monitoring of Pedicle Screw Placement with Computed Tomographic Scan Confirmation", Spine, 20(12):1375-1379 (1995).

Goldstein, et al., "Minimally Invasive Endoscopic Surgery of the Lumbar Spine", Operative Techniques in Orthopaedics, 7(1):27-35 (1997).

Greenblatt, et al., "Needle Nerve Stimulator-Locator: Nerve Blocks with a New Instrument for Locating Nerves", Anesthesia and Analgesia, 41(5):599-602 (1962).

Hinrichs, et al., "A trend-detection algorithm for intraoperative EEG monitoring", Medical Engineering and Physics, 18(8):626-631 (1996).

Holland, "Spine Update, Intraoperative Electromyography During Thoracolumbar Spinal Surgery", Spine, 23(17):1915-1922 (1998).

Holland, et al., "Continuous Electromyographic Monitoring to Detect Nerve Root Injury During Thoracolumbar Scoliosis Surgery", Spine, 22 (21):2547-2550 (1997).

Hovey, "A Guide to Motor Nerve Monitoring," pp. 1-31, The Magstim Company Limited (Mar. 20, 1998).

Isley, et al., "Recent Advances in Intraoperative Neuromonitoring of Spinal Cord Function: Pedicle Screw Stimulation Techniques", 37 (2):93-126, (1997).

Kossmann et al., "The use of a retractor system (SynFrame) for open, minimal invasive reconstruction of the anterior column of the thoracic and lumbar spine" European Spine Journal, 10:396-402 (2001).

Kossmann, et al., "Minimally Invasive Vertebral Replacement with Cages in Thoracic and Lumbar Spine", European Journal of Trauma, 6:292-300 (2001).

Lenke, et al., "Triggered Electromyographic Threshold for Accuracy of Pedicle Screw Placement, An Animal Model and Clinical Correlation", Spine 20(14):1585-1591 (1995).

Maguire, et al., "Evaluation of Intrapedicular Screw Position Using Intraoperative Evoked Electromyography", Spine, 20(9):1068-1074 (1995).

Mathews, et al., "Laparoscopic Discectomy With Anterior Lumbar Interbody Fusion, A Preliminary Review", Spine, 20(16):1797-1802 (1995).

Mayer, "Microsurgical Anterior Lumbar Interbody Fusion (MINI-ALIF)—The Retroperitoneal Approach to L2/3, L3/4, and L4/5," Minimally Invasive Spine Surgery, A Surgical Manual, Chapter 12, pp. 117-131 (2000).

Medtronic, "Nerve Integrity Monitor, Intraoperative EMG Monitor, User's Guide", Medtronic Xomed U.K. Limited, Unit 5, West Point Row, Great Park Road, Almondsbury, Bristol B5324QG, England, pp. 1-39 (2000).

Minahan, et al., "The Effect of Neuromuscular Blockade on Pedicle Screw Stimulation Thresholds" Spine, 25(19):2526-2530 (2000).

(56) References Cited

OTHER PUBLICATIONS

Moller, "Intraoperative Neurophysiologic Monitoring", University of Pittsburgh, School of Medicine Pennsylvania, (1995) by Harwood Academic Publishers GmbH (pp. 217-285).
Pimenta, et al., "Implante de prótese de núcleo pulposo: análise inicial", Jornal Brasilerio De Neurocirurgia, 12 (2):93-96 (2001).
Pimento, et al.,"Endoscopic Approach to the Cervical Spine," 7th World Congress of Endoscopic Surgery, Singapore, Jun. 1-4, 2000 Monduzzi Editore S.p.A.; email: monduzzi@monduzzi.com, pp. 97-103 and 105-111 (also known as Lomanto in 101).
Raymond, et al., "The NerveSeeker: A System for Automated Nerve Localization", Regional Anesthesia 17:151-162 (1992).
Reidy, et al., "Evaluation of electromyographic monitoring during insertion of thoracic pedicle screws", British Editorial Society of Bone and Joint Surgery, 83(7):1009-1014 (2001).
Riordan, "Patents; A businessman invents a device to give laparoscopic surgeons a better view of their work", New York Times www.nytimes.com/2004/29/business/patents-businessman-invents-device-give-la (Mar. 2004).
Rose, et al., "Persistently Electrified Pedicle Stimulation Instruments in Spinal Instrumentation: Technique and Protocol Development", Spine: 22(3):334-343 (1997).
Schick, et al., "Microendoscopic lumbar discectomy versus open surgery: an intraoperative EMG study", European Spine Journal, 11:20-26 (2002).
Toleikis, et al., "The usefulness of Electrical Stimulation for Assessing Pedicle Screw Placements", Journal of Spinal Disorders, 13(4):283-289 (2000).
Traynelis, "Spinal arthroplasty", Neurosurgical Focus, 13(2):1-7 (2002).
Urmey, "Using the nerve stimulator for peripheral or plexus nerve blocks," Minerva Anesthesiology, 72:467-71 (2006).
Vaccaro, et al., "Minimally Invasive Approaches to the Lumbar Spine", Principles and Practice of Spine Surgery, Mosby, Inc., Chapter 21, pp. 275-281 (2003).
Weiss, "Spinal Cord and Nerve Root Monitoring During Surgical Treatment of Lumbar Stenosis," Clinical Orthopaedics and Related Research, 384:82-100 (2001) (also known as Brighton in 101).
Welch, et al., "Evaluation with evoked and spontaneous electromyography during lumbar instrumentation: A prospective study", Journal of Neurosurgery, 87:397-402 (1997).
Zouridakis, et al., "A Concise Guide to Intraoperative Monitoring", Library of Congress card No. 00-046750, Chapter 3, p. 21, chapter 4, p. 58 and chapter 7 pp. 119-120 (Copyright 2001).

\* cited by examiner

APPARATUS, SYSTEM, AND METHOD FOR MAPPING THE LOCATION OF A NERVE

CROSS-REFERENCE TO RELATED APPLICATIONS

This application is a continuation of U.S. patent application Ser. No. 12/913,603 (allowed), filed on Oct. 27, 2010, the disclosure of which is hereby incorporated by reference in its entirety.

FIELD OF THE INVENTION

This invention relates to nerve monitoring and more particularly relates to nerve mapping in three dimensions.

BACKGROUND

Description of the Related Art

Back surgery is increasingly done using minimally invasive methods. Nerves which are exposed during open surgical procedures are usually not visible using a minimally invasive procedure. Nerves which are exposed during minimally invasive methods are subject to damage during such a procedure and care should be taken to avoid touching or damaging a nerve.

SUMMARY

From the foregoing discussion, it should be apparent that a need exists for an apparatus, system, and method to map the location of a nerve. Beneficially, such an apparatus, system, and method would map the location on the nerve in three dimensions.

The present subject matter has been developed in response to the present state of the art, and in particular, in response to the problems and needs in the art that have not yet been fully solved by currently available nerve proximity indication systems. Accordingly, the present subject matter has been developed to provide an apparatus, system, and method for mapping the location of a nerve that overcome many or all of the above-discussed shortcomings in the art.

The apparatus to map the location of a nerve is provided with a plurality of modules configured to functionally execute the necessary steps of stimulating a nerve, detecting a muscle reaction, calculating a distance between a stimulation electrode and a nerve, and mapping the location of a nerve using at least two distance calculations. These modules in the described embodiments include at least one stimulation electrode, a stimulation detection module, a distance module, and a mapping module.

In certain embodiments the at least one stimulation electrode stimulates a nerve with an electrical stimulation current from an electrical source. In one embodiment a stimulation detection module detects a muscle reaction resulting from stimulation of the nerve by the at least one stimulation electrode. The distance module may use information from the at least one stimulation electrode and from the stimulation detection module to calculate a distance between the at least one stimulation electrode and the nerve. The mapping module maps a location on the nerve using at least two distances calculated by the distance module and position information of the at least one stimulation electrode for each of the at least two distances calculated. In one embodiment the map of the location on the nerve indicates a location of a point on the nerve.

In certain embodiments the stimulation detection module includes an electromyograph that detects an electrical potential generated by a muscle cell in response to stimulation of the nerve by the at least one stimulation electrode.

In one embodiment the at least two distances calculated by the distance module includes at least three distances. In certain embodiments each distance calculated indicates a spherical locus of potential sites or the nerve equidistant from a position of the at least one stimulation electrode when the at least one stimulation electrode stimulates the nerve. In one embodiment the mapping module maps the location on the nerve by determining an intersection of the spherical locus of potential sites.

The at least one stimulation electrode, in one embodiment, includes a first stimulation electrode, a second stimulation electrode, and a third stimulation electrode. In certain embodiments the first stimulation electrode stimulates the nerve from a first position to calculate a first distance. The second stimulation electrode, in certain embodiments, stimulates the nerve from a second position to calculate a second distance. The third stimulation electrode stimulates the nerve from a third position to calculate a third distance. In one embodiment the mapping module maps a first location on the nerve using the first distance, the second distance, and the third distance. In one embodiment, the calculated distance may be elliptical or some other non-spherical shape based on the electrical field associated with each electrode.

The apparatus, in certain embodiments, includes an electrode positioning module that moves at least one of the first stimulation electrode, the second stimulation electrode, and the third stimulation electrode to a new position. In one embodiment, at each new position of a stimulation electrode, the stimulation detection module, the distance module, and the mapping module determine one or more additional locations on the nerve. In certain embodiments the mapping module maps a route of the nerve using the one or more additional locations on the nerve.

In a further embodiment, the electrode positioning module moves the first stimulation electrode, the second stimulation electrode, and the third stimulation electrode to obtain additional distance calculations and map one or more additional locations on the nerve.

The at least one stimulation electrode, in one embodiment, includes a single stimulation electrode and also includes an electrode positioning module. The electrode positioning module positions the stimulation electrode in at least three positions to calculate at least three distances using the stimulation electrode and the distance module.

In certain embodiments, the electrode positioning module moves the stimulation electrode to a new position to determine one or more additional locations on the nerve using the stimulation electrode, the stimulation detection module, the distance module, and the mapping module. In one embodiment the mapping module maps a route of the nerve using the one or more additional locations on the nerve.

The apparatus, in certain embodiments, also includes an imaging module and an overlay module. The imaging module captures an image of a patient's anatomy. The overlay module, in one embodiment, overlays a map of the location of the nerve on the image of the patient's anatomy. In certain embodiments the image is captured by the imaging module and the map is mapped by the mapping module.

In a further embodiment the apparatus also includes a marking module. The marking module, in one embodiment, marks a position of the at least one stimulation electrode with a marker. The marker may be made of a material detectable by the imaging module. The overlay module, in one embodiment, uses the marker to position the map of the location on the nerve on the image of the patient's anatomy captured by the imaging module.

In certain embodiments the imaging module captures a three dimensional image of the patient's anatomy. In one embodiment the overlay module overlays the map of the location on the nerve in three dimensions such that the location on the nerve within the patient's anatomy is identified in three dimensions. The imaging module, in certain embodiments, includes one or more of an imaging device selected from an x-ray device, a computerized axial tomography device, a magnetic resonance imaging device, and an ultrasound device.

A method of the present subject matter is also presented for mapping the location of a nerve. The method in the disclosed embodiments substantially includes the steps necessary to carry out the functions presented above with respect to the operation of the described apparatus and system. In one embodiment, the method includes stimulating a nerve with a stimulation current from an electrical source using at least one stimulation electrode.

The method also may include detecting a muscle reaction resulting from stimulation of the nerve by the at least one stimulation electrode. In certain embodiments a distance between the at least one stimulation electrode and the nerve is calculated using current information from the at least one stimulation electrode at a time of first detecting the muscle reaction. The method includes other methods of detecting the nerve stimulation using a nerve response, a spinal cord response, or a somato-sensory response. The method also includes stimulating one or more peripheral nerves distal to the spinal cord and using the multiple electrodes as pickup electrodes for the resulting nerve activity.

The method may also include mapping a location on the nerve using at least two distances calculated and position information of the at least one stimulation electrode for each of the at least two distances calculated. In a further embodiment, the mapping of the location on the nerve includes determining an intersection of a spherical locus of potential sites of the nerve equidistant from a position of the at least one stimulation electrode when the at least one stimulation electrode stimulates the nerve.

In one embodiment, the at least two distances calculated includes at least three distances. Each of the at least three distances calculated indicates a spherical locus of potential sites of the nerve equidistant from a position of the at least one stimulation electrode when the at least one stimulation electrode stimulates the nerve. In one embodiment the location on the nerve is determined by determining an intersection between the spherical locus of potential sites indicated by the at least three distances.

In a further embodiment an image of the patient's anatomy may be captured and a map of the location of the nerve may be overlaid on the image of the patient's anatomy.

Reference throughout this specification to features, advantages, or similar language does not imply that all of the features and advantages that may be realized with the subject matter should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Furthermore, the described features, advantages, and characteristics of the subject matter may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments.

These features and advantages of the present subject matter will become more fully apparent from the following description and appended claims, or may be learned by the practice of the subject matter as set forth hereinafter.

BRIEF DESCRIPTION OF THE DRAWINGS

In order that the advantages will be readily understood, a more particular description of the subject matter briefly described above will be rendered by reference to specific embodiments that are illustrated in the appended drawings. Understanding that these drawings depict only typical embodiments and are not therefore to be considered to be limiting of its scope, the subject matter will be described and explained with additional specificity and detail through the use of the accompanying drawings, in which.

DETAILED DESCRIPTION

Figure 1:
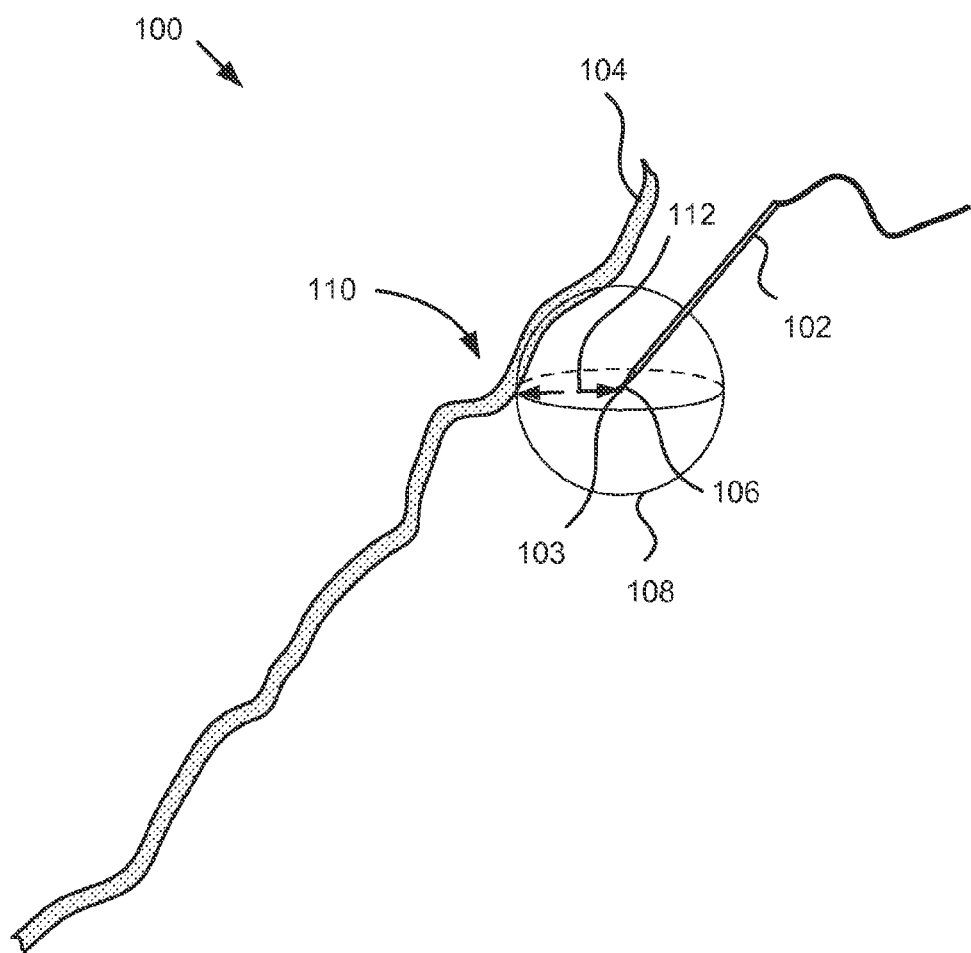
FIG. 1 depicts a side view of one embodiment of a system for mapping the location of a nerve using a single stimulation electrode.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

Furthermore, the described features, structures, or characteristics of the subject matter may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the subject matter.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

One of skill in the art will recognize that an electrical current applied to a nerve initiates a muscle contraction. Further, one of skill in the art will recognize that during voluntary as well as involuntary contraction a muscle cell creates an observable electrical potential. By stimulating a nerve with an electrical current from a stimulation electrode the muscle cells that the stimulated nerve innervates will create an electrical potential. Nerves are sensitive to electrical stimulation and the amount of charge needed to depolarize a nerve can be used to estimate the distance of the nerve from the stimulating electrode. Nerve depolarization may be measured indirectly by detecting electromyogram activity in a muscle associated with the nerve.

Dilators and other surgical instruments which are inserted and used to cut or stretch tissue may be equipped with stimulating sites to induce art electromyogram response in a muscle associated with a nerve. An electromyogram response in a muscle associated with a nerve may indicate nerve proximity but the practitioner is left to guess as to the location of the nerve.

The subject matter of the present disclosure is directed to a nerve mapping system, method and apparatus that generates a virtual three dimensional view of a nerve or nerves. The three dimensional view can be used to guide a dilator or other surgical instrument past vulnerable nerve roots.

Nerve depolarization is an 'all or none' phenomenon. A peripheral nerve contains hundreds to thousands of neurons, each of which fires tens to thousands of muscle fibers. Electrical depolarization occurs abruptly when enough total charge is forced across an individual neuron, and each neuron that is depolarized adds to an electromyogram response.

Using established models for nerve depolarization, and established models for electrical fields in volume conductors, the present subject matter allows the computation of a distance from a stimulus site to a nerve as a function of other variables that can be either controlled or estimated.

The primary nerve characteristic of interest is its depolarization charge. A nerve's depolarization charge varies across individual neurons hut has a statistically well-defined distribution. The minimal charge for the first few neurons to depolarize is well-defined and repeatable.

A charge delivered to a nerve from a stimulation electrode is a function of several variables. Including (1) the stimulator output level, (2) the stimulus duration and polarity, (3) the absolute distance from the stimulation electrode, and (4) the orientation of the field in the sense of a three axis vector.

FIG. 1 depicts one embodiment of a system 100 for mapping the location of a nerve 104 using a single stimulation electrode 102 positioned at a first position 103. With a stimulation electrode 102 positioned at a first position 103, the distance 112 between a tip 106 of the stimulation electrode 102 and the nerve 104 can be measured by adjusting the stimulation current provided to the tip 106 of the stimulation electrode 102 until a threshold electromyogram response is detected in a muscle located some distance away from the stimulation site. In certain embodiments the stimulation current may be adjusted or controlled through the use of a second stimulation electrode (not shown), an indifferent electrode (not shown), or in combination.

In certain embodiments the muscle or muscles exhibiting the threshold electromyogram response may give a skilled practitioner additional insight into which of several nerves 104 is being stimulated. In certain embodiments knowledge of human anatomy will give one of ordinary skill in the art insight into the route a particular nerve 104 typically takes within a human body.

Typically, the larger the distance 112 between the stimulation electrode 102 and the nerve 104 the higher the stimulation current required to elicit an electromyogram response in the muscle. In one embodiment Coulombs law, also known as the inverse problem for source localization, may be used to determine the distance 112 between the stimulation electrode 102 and the nerve 104. In other embodiments other formula's may be used to determine the distance 112 between the stimulation electrode 102 and the nerve 104 as a function of a stimulation current required to invoke an electromyogram response in the muscle.

The applicable form of Coulombs law can be expressed mathematically as $Q=k(Q_0/r^2)$ where Q is the required stimulating charge. K is a function of the nerve, $Q_0$ is the minimum charge needed to stimulate the nerve 104, and r is the distance 112 between the stimulation electrode 102 and the nerve 104 (represented in FIG. 1 as the distance between the tips of the arrow 112). Therefore, one of skill in the art will recognize that where the required stimulating charge E and the minimal charge needed to stimulate the nerve 104 are known, the distance r (112) between the stimulation electrode 102 and the nerve 104 can be calculated. The stimulating current and charge are related by the stimulus duration which is generally fixed. Use of the term "stimulating current" is used hereafter.

One of skill in the art will recognize that variables such as an impedance level of the tissue surrounding the tip 106 of the stimulation electrode 102, the nerve geometry, the stimulation electrode 102 characteristics, stimulation electrode 102 geometry, whether or not the stimulation electrode 102 is used as the anode or cathode, etc. may affect the accuracy of the distance calculation. One of ordinary skill of one in the art may account for these external variables in making the distance calculations.

In certain embodiments a single stimulation electrode 102 used to determine the distance 112 between the stimulation electrode 102 and the nerve 104 gives an absolute distance using Coulomb's law discussed above. While the distance 112 between the stimulation electrode 102 and the nerve 104 may be determined, the calculation may typically be interpreted as a spherical locus of potential sites 108 of the nerve 104 equidistant from a position (in this case the first position 103) when the stimulation electrode 102 stimulates the nerve 104. The direction of the nerve 104 from the stimulation site at the tip 106 of the stimulation electrode 102 is typically unknown.

After a single distance has been determined, the calculation indicates that the nerve 104 may be located anywhere on the spherical focus of potential sites 108. Thus, while stimulation current may actually stimulate the nerve 104 at the interface 110 between the stimulation current and the nerve 104, the distance calculation typically only indicates that the nerve 104 is a certain distance away from the stimulation site which may be any point on the spherical locus of potential sites 108.

Figure 2:
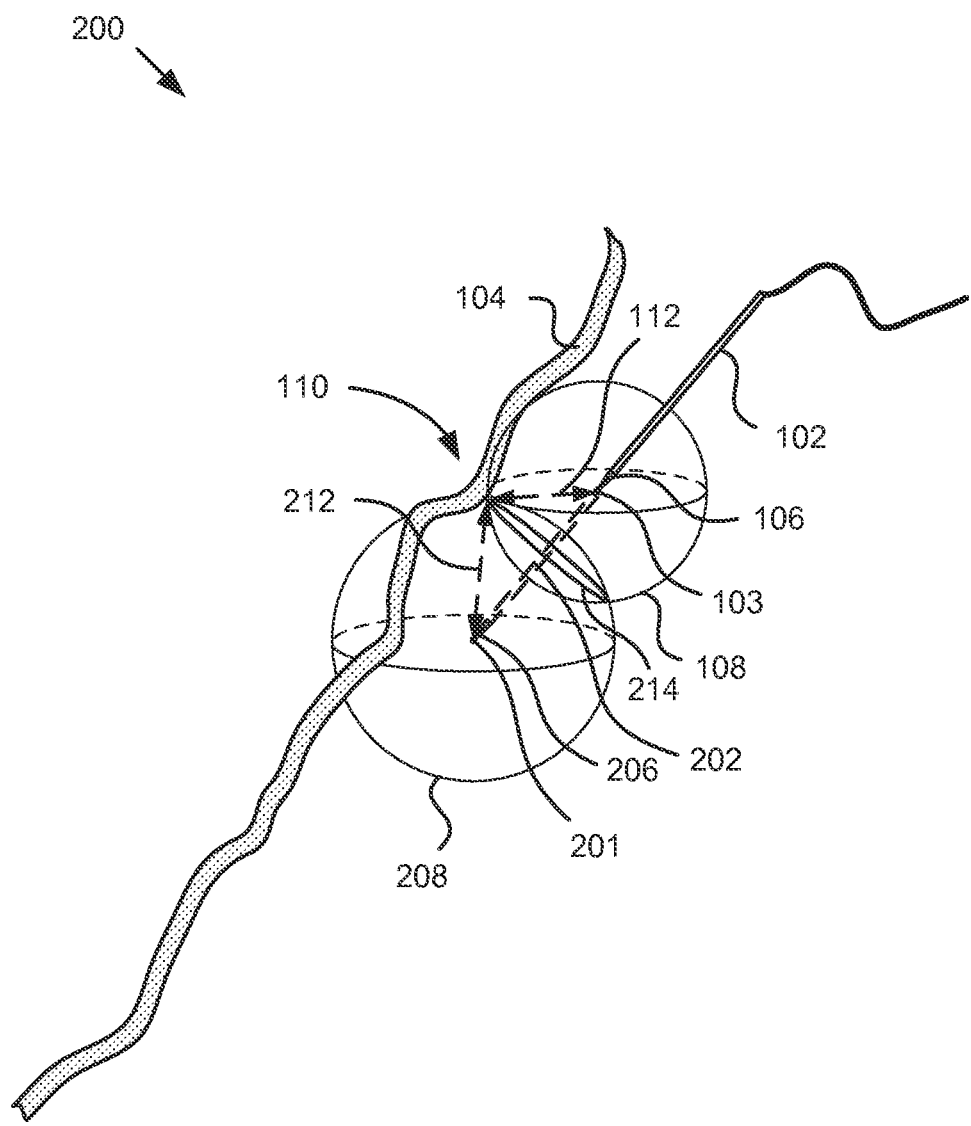
FIG. 2 depicts a side view further illustrating one embodiment of the system for mapping the location of a nerve using a single stimulation electrode of FIG. 1 with the stimulation electrode repositioned to a second position.

FIG. 2 depicts one embodiment of a system 200 for mapping the location of a nerve 104 using a single stimulation electrode 102 which is positioned at a first position 103 and then repositioned to a second position 201. In the embodiment illustrated in FIG. 2, the repositioned stimulation electrode 202 is illustrated in a dashed outline indicating that the stimulation electrode 102 has been repositioned to the second position 201.

Using the repositioned stimulation electrode 202 positioned at the second position 201, the distance 212 between the tip 206 of the repositioned stimulation electrode 202 and the nerve 104 can be measured by adjusting the stimulation current provided to the tip 206 of the repositioned stimulation electrode 202 until a threshold electromyogram response is detected in the muscle located some distance away from the stimulation site.

The stimulation current I required to invoke the threshold electromyogram response with the repositioned stimulation electrode 202 positioned in the second position 201 can be used to calculate a distance 212 between the tip 206 of the repositioned stimulation electrode 202 and the nerve 104 using Coulomb's law discussed above. Again, the calculation of the distance 212 between the tip 206 of the repositioned stimulation electrode 202 and the nerve 104 may be interpreted as a spherical locus of potential sites 208 with each site equidistant from the stimulation site at the tip 206 of the repositioned stimulation electrode 202. Thus, the nerve 104 may be located at any position on the spherical locus of potential sites 208.

If the first position 102 of the tip 106 of the stimulation electrode 102 and the second position 201 of the tip 206 of the repositioned stimulation electrode 202 are known, an estimation of the actual location of the nerve 104 can be narrowed to a position falling somewhere on the intersection of spherical locus of potential sites 108 and spherical locus of potential sites 208 which is a circle 214. Thus, in certain embodiments, where a single stimulation electrode 102 is used to determine two distances, the position of the nerve 104 may typically be pinpointed with an accuracy of circle 214.

While the embodiment illustrated in FIG. 2 depicts the stimulation electrode 102 as being repositioned along an axis of the stimulation electrode 102, one of skill in the art will recognize that the stimulation electrode 102 may also be repositioned in a direction transverse to the axis of the stimulation electrode 102 to obtain distance calculations between the tip 106 of the stimulation electrode 102 and the nerve 104. Using a single stimulation electrode 102 in this manner, the user is generating a mental image of the nerve 104 by probing forward and back and side to side and turning the stimulation current up and down to determine a distance between the tip 106 of the stimulation electrode 102 and the nerve 104 at various locations.

In certain embodiments the two distances calculated, the first being the distance calculated between the tip 106 of the stimulation electrode 102 and the nerve 104 with the stimulation electrode 102 positioned at the first position 103, and the second being the distance calculated between the tip 206 of the repositioned stimulation electrode 202 and the nerve 104 with the repositioned stimulation electrode 202 positioned at the second position 201, may be enough, to determine a position of the nerve 104. For example, in highly uniform nerves 104, that is, with nerves 104 that do not typically vary significantly in location from patient to patient, only one location on the circle 214 or a section of the circle 214 may make sense to one of skill in the art and other locations on the circle 214 may be ruled out as a possible location of the nerve 104. A section of the circle 214, in one embodiment, may be accurate enough for the purposes of a procedure. In one embodiment a precise calculation of a location of a nerve 104 may not be necessary. In such an embodiment knowing that the nerve 104 lies somewhere on the circle 214 may be enough to perform certain medical procedures.

In other embodiments additional distance calculations may be performed with the stimulation electrode 102 positioned at three or more positions within a patient. A third distance calculation, with the stimulation electrode 102 positioned at a third position, may map the position on the nerve 104 to two points on circle 214 as further discussed with reference to FIG. 3.

Typically a nerve 104 is a chord-like structure that may run throughout a patient's body to control various muscle functions in the patient. Therefore, one of skill in the art will recognize mat in certain embodiments the phrase "position on the nerve" may be used to indicate a point on the nerve 104 and not necessarily the entire chord-like structure of the nerve 104. As discussed below. In certain embodiments additional points or positions on the nerve 104 may be determined using the methods, apparatuses and systems described herein to map a path or route of the nerve 104 as it passes through the patient's anatomy.

While the embodiments discussed thus far have been described with reference to the stimulation electrode 102 positioned within a patient, one of skill in the art will recognize that in certain embodiments the stimulation electrode 102 may be a surface electrode positioned on a surface of the patient's skin.

Figure 3:
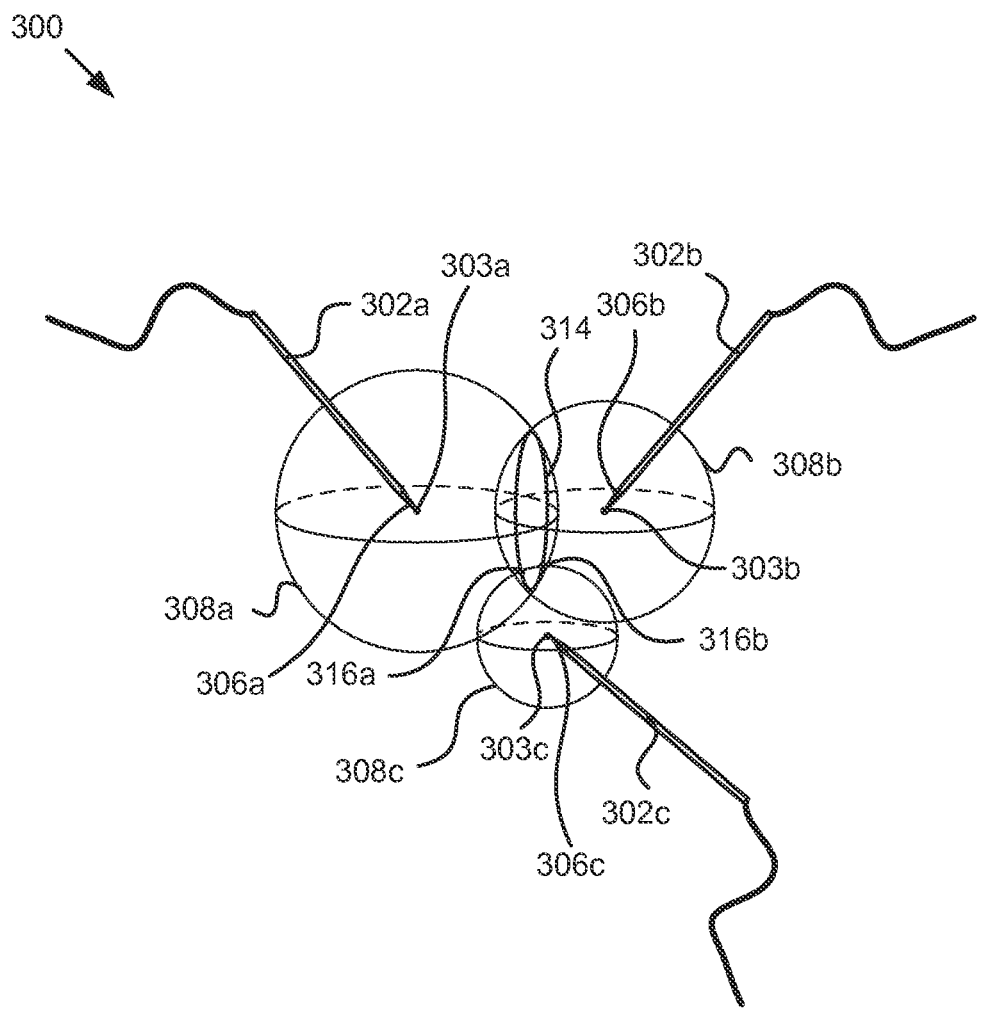
FIG. 3 depicts a side view of one embodiment of a system for mapping the location of a nerve using multiple stimulation electrodes.

FIG. 3 depicts one embodiment of a system 300 for mapping the location of a nerve 104 using three stimulation electrodes 302 which are positioned at three positions 303. While the embodiment illustrated in FIG. 3 depicts three separate stimulation electrodes 302, one of skill in the art will recognize that in certain embodiments a single electrode 302 may be used and repositioned to three different positions 303. In the embodiment illustrated in FIG. 3, the nerve 104 has been omitted for clarity.

In certain embodiments the stimulation electrodes 302 may be positioned on or within a patient at three separate positions 303. Each stimulation electrode 302 may then deliver a stimulation current I to the patient. In certain embodiments the stimulation current I may be increased until a threshold electromyogram response is observed in a muscle. In one embodiment the stimulation current I is delivered to each stimulation electrode 302 one at a time so that a practitioner can determine which of the three stimulation electrodes 302 is evoking the threshold electromyogram response. In other embodiments the stimulation current may be delivered to two or more of the stimulation electrodes 302 at the same time.

In certain embodiments, once the stimulation current required to invoke the threshold electromyogram response in the muscle for each stimulation electrode 302 is determined, Coulomb's law may be used to calculate the distance between each stimulation electrode 302 and the nerve 104 (FIGS. 1 and 2). Each distance calculated may be interpreted as a spherical locus of potential sites 308 of the nerve 104 equidistant from a position 303 of the stimulation electrode 302 when the stimulation electrode 302 stimulates the nerve 104.

As discussed above, if the position 303 of the stimulation electrodes 302 are known, an estimation of the actual location of the nerve 104 may be narrowed to a position falling somewhere on an intersection of two of the spherical locus of potential sites (in this case the intersection of spherical locus of potential sites 308a and 308b) which is a circle 314. An intersection of the circle 314 and a third spherical locus of potential sites 308c may be used to pinpoint the location of the nerve 104 to two positions 316 on the circle 314 as defined by the intersection of spherical locus of potential sites 308a and 308b.

In certain embodiments pinpointing the location of the nerve 104 to one or two positions 316 on the circle 314 defined by the intersection of spherical locus of potential sites 308a and 308b may give a practitioner sufficient resolution to perform a surgical or other medical procedure. In other embodiments additional distance calculations may be performed, either with additional stimulation electrodes 302 or by repositioning one of the stimulation electrodes 302, to give the practitioner greater insight into the position of the nerve 104.

Figure 4:
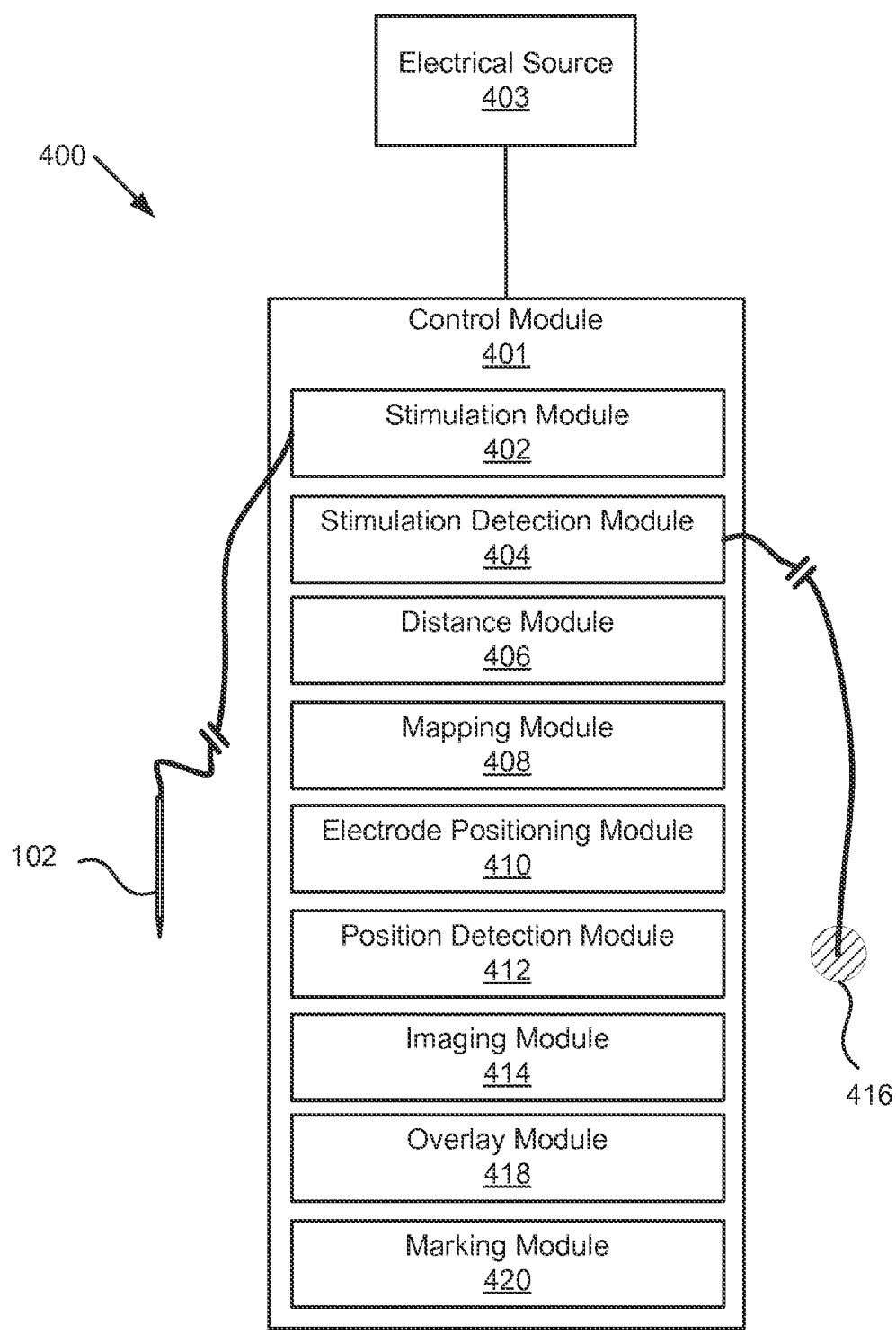
FIG. 4 depicts a block diagram of one embodiment of an apparatus 400 to map the location of a nerve.

FIG. 4 depicts a block diagram of one embodiment of an apparatus 400 to map the location of a nerve such as nerve 104 of FIGS. 1 and 2. The apparatus 400 may include at least one stimulation electrode 102, at least one electromyogram pickup electrode 416, and a control module 401. In one embodiment the control module 401 includes a stimulation module 402, a stimulation detection module 404, a distance module 406, and a mapping module 408. In certain embodiments the control module 401 may also include an electrode positioning module 410, a position detection module 412, an imaging module 414, an overlay module 418, and a marking module 420.

In certain embodiments the stimulation module 402 stimulates a nerve 104 with an electrical stimulation current from at least one stimulation electrode 102. In one embodiment the stimulation current is provided by an electrical source 403. In certain embodiments the electrical source 403 may be internal to the apparatus 400, that is, in one embodiment the apparatus 400 may include an internal electrical source 403 such as a battery. In other embodiments the electrical source 403 may be external to the apparatus 400.

In one embodiment the stimulation electrode(s) 102 may be directly electrically coupled to the electrical source 403. In such an embodiment the stimulation electrode(s) 102 may provide feedback to the control module 401 for use in determining the location of a nerve 104. In certain embodiments feedback from the stimulation electrode(s) 102 may include one or more of position information identifying a position of the stimulation electrode(s) 102 when the stimulation electrode(s) 102 is stimulating a nerve 104, information about the amplitude of the stimulation current delivered to the stimulation electrode(s) 102, information about the frequency of the stimulation current delivered to the stimulation electrode(s) 102, information regarding the timing of the stimulation current delivered to the stimulation electrode(s) 102, etc.

In other embodiments the electrical source 403 may be coupled to the control module 401 and the control module 401 may provide an electrical current from the electrical source 403 to the stimulation electrode(s) 102. In such an embodiment the control module 101 may control the position of the stimulation electrode(s) 102 with an electrode positioning module 410, the amplitude of the stimulation current delivered to the stimulation electrode(s) 102, the frequency of the stimulation current delivered to the stimulation electrode(s) 102, and/or information regarding the timing of the stimulation current delivered to the stimulation electrode(s) 102. Thus, in certain embodiments feedback, from the stimulation electrode(s) 102 may be unnecessary as the control module 401 may already have such information by virtue of the control module 401 controlling the amplitude, frequency, and timing of the stimulation current as well controlling the position of the stimulation electrode(s) 102.

The stimulation detection module 404 detects a muscle reaction. In one embodiment the muscle reaction includes a response in a muscle resulting from stimulation of the nerve by the at least one stimulation electrode 102.

In certain embodiments the stimulation detection module 404 may include an electromyograph coupled to an electromyogram pickup electrode 416, directly, through the control module 401, through another module, or the like. The electromyogram pickup electrode 416 detects an electric potential generated by a muscle cell or group of muscle cells in response to stimulation of the nerve 104 by the at least one stimulation electrode 102. In certain embodiments the electromyogram pickup electrode 416 may be a surface electrode or electrodes. In other embodiments the electromyogram pickup electrode 416 may be an intramuscular electrode or electrodes positioned within the muscle tissue of the patient.

In one embodiment a physician, technician or other user may visually observe a muscle response caused by the stimulation electrode 102 stimulating the nerve 104 with the stimulation current. In such an embodiment the electromyograph may be unnecessary and may be omitted or may supplement physical observations.

The distance module 406, in one embodiment, uses information from the stimulation module 402 and from the stimulation detection module 404 to calculate a distance 112 between the stimulation electrode 102 and the nerve 104. In certain embodiments the information from the stimulation module 402 includes information about the threshold current that causes a muscle reaction. The information from the stimulation detection module 404 may include information about which muscle reacted to stimulation of the nerve 104 by the stimulation electrode 102. In one embodiment the information from the stimulation detection module 404 may simply include information indicating that a muscle responded, regardless of which muscle responded.

For example, in certain embodiments the stimulation electrode 102 is positioned on or within a patient. A stimulation current is provided through the stimulation electrode 102 and is increased until the stimulation detection module 404 detects a threshold response in a muscle, either through visual observation or by the electromyograph. Once a threshold response is observed, the stimulation current required to invoke the threshold response in the muscle may be used to calculate a distance 112 between the stimulation electrode 102 and the nerve 104.

In one embodiment the distance module 406 may use Coulomb's equation discussed above to calculate the distance 112 between the stimulation electrode 102 and the nerve 104. In other embodiments other formula's may be used to determine the distance 112 between the stimulation electrode 102 and the nerve 104 as a function of a stimulation current required to invoke an electromyogram response in the muscle.

The mapping module 408, in one embodiment, maps a location on the nerve 104 using at least three of the distances calculated by the distance module 406. In certain embodiments the mapping module 408 also uses position information of the stimulation electrode 102 to map the location on the nerve 104.

For example, referring again to FIG. 3, in certain embodiments the distance module 406 calculates a series of distances for each position 303 of the stimulation electrodes 302. The distances calculated indicate a spherical locus of potential sites 308 of the nerve 104 equidistant from a position 303 of the stimulation electrode 302 when the stimulation electrode 302 stimulates the nerve 104.

In the embodiment illustrated in FIG. 3 there are three stimulation electrodes 302, a first stimulation electrode 302a, a second stimulation electrode 302b, and a third stimulation electrode 302c. The first stimulation electrode 302a stimulates the nerve 104 from a first position 303a to calculate a first distance. The second stimulation electrode 302b stimulates the nerve 104 from a second position 303b to calculate a second distance. The third stimulation electrode 302c stimulates the nerve 104 from a third position 303c to calculate a third distance.

The mapping module 408 maps a first location on the nerve 104 using the first distance, the second distance, and the third distance. In certain embodiments the mapping module 408 uses a known position of each stimulation electrode 302 (or a single stimulation electrode 102) to determine where the spherical loci of potential sites 308 overlap.

In certain embodiments the position detection module 412 may know the position of each stimulation electrode 302 (or a single stimulation electrode 102) by virtue of an electrode positioning module 410 controlling the position of each stimulation electrode 302 (or a single stimulation electrode 102).

In other embodiments the position of each stimulation electrode 302 (or a single stimulation electrode 102) may be known to the position detection module 412 by virtue of feedback information provided by the stimulation electrodes 302 (or the single stimulation electrode 102) to the position detection module 412. One of skill in the art will recognize that the position information of the stimulation electrodes 302 (or the single stimulation electrode 102) may only be relevant where the position information relates to the position of the stimulation electrodes 302 (or the single stimulation electrode 102) when the stimulation electrodes 302 (or the single stimulation electrode 102) is stimulating the nerve 104.

As discussed above, the intersection of three spherical loci of potential sites 308 may result in two potential two positions 316 on the circle 314 where the nerve 104 may be located. In other embodiments the mapping module 408 may use more than three distance calculations to more precisely identify the location on the nerve 104.

In certain embodiments the apparatus 400 may include an electrode positioning module 410. The electrode positioning module 410 may position the stimulation electrodes 302 (or the single stimulation electrode 102) in position to calculate a first set of distances between the tip 306 of each stimulation electrode 302 (or the tip 106 of the single stimulation electrode) and the nerve 104. These distances may be used by the mapping module 408 to map the location on the nerve 104.

In one embodiment the electrode positioning module 410 moves at least one of the first stimulation electrode 302a, the second stimulation electrode 302b, and the third stimulation electrode 302c to a new position. At each new position of a stimulation electrode 302, the stimulation detection module 404, the distance module 406, and the mapping module 408 may be used to determine one or more additional locations on the nerve 104. In certain embodiments the additional locations may be determined in a manner substantially similar to the manner in which the first location on the nerve 104 is determined.

In one embodiment the electrode positioning module 410 moves the first stimulation electrode 302a, the second stimulation electrode 302b, and the third stimulation electrode 302c. The stimulation electrodes 302 may be moved individually or in unison. At each new position the distance module 406 may calculate a new distance in a manner substantially similar to the manner in which the distance module 406 calculates the original distances. The mapping module 408 may then use new distance, along with two other distances, either the original distances or new distance calculated for each stimulation electrode 302, to map an additional location on the nerve 104.

In another embodiment, such as where the apparatus 400 includes a single stimulation electrode 102, the electrode positioning module 410 may position the stimulation electrode 102 in three positions to calculate three distances using the stimulation electrode 102 and the distance module 406. In certain embodiments the electrode positioning module 410 may move the stimulation electrode 102 to fourth position to determine one or more additional locations on the nerve 104 using the stimulation electrode 102, the distance module 406, and the mapping module 408. In this manner, every time the stimulation electrode 102 is moved, a new distance may be calculated which can be used by the mapping module 408 to map a new location on the nerve 104.

In one embodiment the mapping module 408 may map a route of the nerve 104 as it passes through a patient's body using one or more additional locations on the nerve 104. For example, in certain embodiments a first location, on the nerve 104 may first be mapped by the mapping module 408 using three distances calculated by the distance module 406 as outlined above. One or more of the stimulation electrodes 302 (or the single stimulation electrode 102) may then be repositioned, by the electrode positioning module 410 and a new distance may be calculated by the distance module 406. In other embodiments the electrode positioning module 410 may reposition all three stimulation electrodes 302 to get three new distance calculations. In yet another embodiment the electrode positioning module 410 may reposition a single stimulation electrode 102 at an additional three positions to calculate three additional distances.

In certain embodiments the mapping module 408 may then use the new distance calculation along with two of the original distance calculations to map an additional location on the nerve 104. In other embodiments the mapping module 408 may use the three-new distance calculations to map an additional location on the nerve 104.

A line connecting the first location on the nerve 104 and the additional location on the nerve 104 may indicate a route of the nerve 104 as it passes between the first location and the additional location. In certain embodiments mathematical procedures for finding the best fitting curve, such as least squares fitting between the first location and the second location, may be used to determine the route of the nerve 104.

While the embodiments discussed with relation to apparatus 400 include three distance calculations, one of skill in the art will recognize that in certain embodiment's one or two distance calculations may give a practitioner enough information to locate a nerve 104. Thus, in certain embodiments a single distance or two distance calculations may be used to map the position of the nerve 104 where resolution is not as important. In other embodiments more than three distance calculations may be used to map the location of a nerve 104.

In one embodiment the apparatus 400 may include an imaging module 414 that captures an image of a patient's anatomy. In certain embodiments the imaging module 414 may include one or more of an x-ray device, a computerized axial tomography device, a magnetic resonance imaging device, and an ultrasound device or any other device that Captures an image of a patient's anatomy which is known in the art. In certain embodiments the imaging module 414 may capture a three dimensional image of the patient's anatomy by capturing an image of the patient's anatomy from at least two angles.

In certain embodiments an overlay module 418 overlays a map of the location of the nerve 104 mapped by the mapping module 408 on the image of the patient's anatomy captured by the imaging module 414. Where the image captured by the imaging module 414 is a three dimensional image, the overlay module 418 may overlay the map of the location on the nerve 104 using x, y, and z coordinates of a Cartesian coordinate system such that the location on the nerve 104 within a patient's anatomy is identified in three dimensions. With the nerve 104 mapped in three dimensional space a physician or other practitioner can safely avoid damaging the nerve 104 during a surgical or other medical procedure.

In one embodiment a marking module 420 marks a position of the stimulation electrodes 302 (or the single stimulation electrode 102) with a marker. In certain embodiments the marker is made of a material detectable by the imaging module 414. The overlay module 418 may use the marker to position the map of the location on the nerve 104 on the image of the patient's anatomy captured by the imaging module 444. In certain embodiments the stimulation electrodes 302 (or the single stimulation electrode 102) may be made of a material detectable by the imaging module 414. In other embodiments a separate marker made of a material detectable by the imaging module 414 may be used to mark the position of the stimulation electrodes 302 (or the single stimulation electrode 102).

Figure 5:
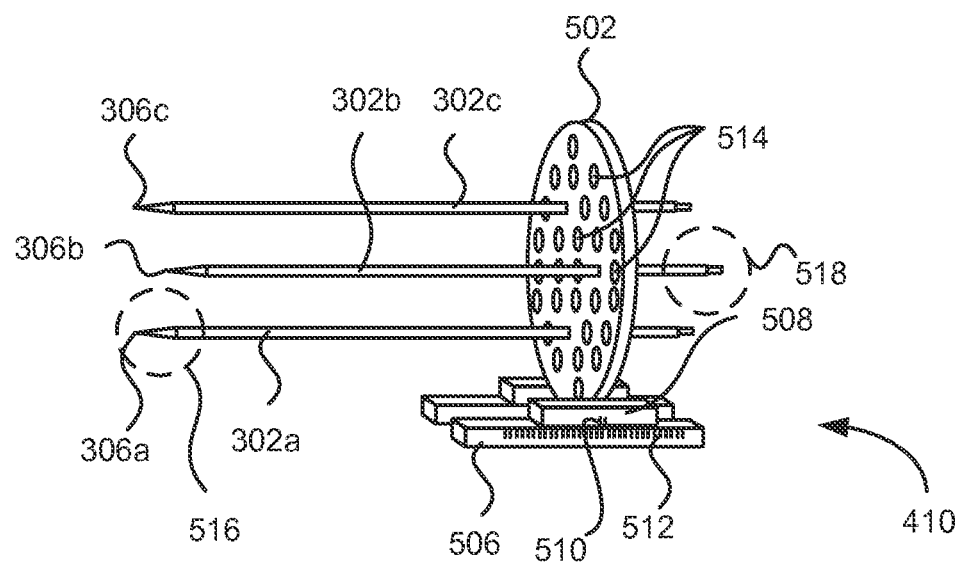
FIG. 5 depicts a side view further illustrating one embodiment of the electrode positioning module of FIG. 4.

FIG. 5 depicts one embodiment of the electrode positioning module 410 of the system 400 of FIG. 4. In certain embodiments the electrode positioning module 410 includes a stimulation electrode mounting member 502, a rigid mount 506, and a slideable coupling 508.

In one embodiment the stimulation electrodes 302 extend through and are mounted to the electrode mounting member 502. The stimulation electrodes 302, in certain embodiments, are rigidly mounted to the electrode mounting member 502. In other embodiments the stimulation electrodes 302 may be slideably mounted to the electrode mounting member 502 such that each stimulation electrode 302 may be individually positioned to a deeper or shallower position within a patient's anatomy.

In embodiments where the stimulation electrodes 302 are rigidly mounted to the electrode mounting member 502 the electrode positioning module 410 may operate to control the depth of the electrodes within a patient's anatomy. The electrode mounting member 502 may be coupled to the slideable coupling 508. In one embodiment, the slideable coupling 508 slides along rigid mount 506 to position or reposition the stimulation electrodes 302 within rise patient's anatomy.

In certain embodiments the electrode positioning module 410 may include a manual adjusting member (not shown) that allows a physician or other user to manually adjust a depth of the stimulation electrodes 302. In such and embodiment the slideable coupling 508 may include depth indicators 510 which correspond with depth indicators 512 located on the rigid mount 506. The depth indicators 510, 512 may be used to give a physician or other operator and indication of the depth of the stimulation electrodes 302 within the patient's anatomy.

In other embodiments the electrode positioning module 410 may be coupled to the control module 401 of apparatus 400 and the control module 401 may control the depth of the stimulation electrodes 302. In such an embodiment the electrode positioning module 410 may include a mechanical adjusting member (not shown) that adjusts the depth of the stimulation electrodes 302. One of skill in the art will recognize that the mechanical adjusting member (not shown) may be incorporated into the electrode positioning module 410 in a variety of different configurations.

In certain embodiments the electrode positioning module 410 allows the user to advance the electrodes 302 into a patient's anatomy in a stepwise fashion. Thus, the electrode positioning module 410 may first position the stimulation electrodes 302 in the patient. The threshold stimulation current required to invoke an electromyogram response may then be determined for each stimulation electrode 302 and the distance module 406 may convert the threshold stimulation current data into distances as described above. The mapping module 408 may use the distance calculations, along with the position information of each stimulation electrode 302 to map a location on the nerve 104. In certain embodiments the electrode positioning module 410 may then reposition the stimulation electrodes 302 and the process just described may be repeated to snap an additional location on the nerve 104.

In certain embodiments the electrode positioning module 410 may assist the position detection module 412 in determining the position of the stimulation electrodes 302 when the stimulation electrodes 302 are positioned within a patient. For example, if the distance between the electrode mounting member 502 and the tip 306 of a particular stimulation electrode 302 is known, and the angle at which the stimulation electrode 302 is inserted into a patient's anatomy also known, the location of the tip 306 of the stimulation electrode 302 relative to the electrode mounting member 502 can be determined.

In one embodiment the electrode mounting member 502 includes a number of guide holes 514 for guiding a physician or other user in positioning a dilator, needle, or other surgical or medical instrument within a patient's anatomy. In certain embodiments, once the location of a nerve 104 or the route of the nerve 104 has been mapped, the stimulation electrodes 302 may remain positioned within the patient. The physician or other user may use the stimulation electrodes 302 as a reference of where to position the surgical or other medical instrument and may select a guide hole 514 that will guide the surgical or other medical instrument into the patient's anatomy without interfering with or damaging the nerve 104. In certain embodiments the guide holes 514 may be replaced with a multi-axis aiming system that guides a physicians placement of the surgical or other medical instrument.

In the embodiment illustrated in FIG. 5 three stimulation electrodes 302 are mounted to the substantially rigid mounting member 504 in a triangular pattern. In other embodiments mom than three stimulation electrodes 302 may be mounted to the substantially rigid mounting member 504 in a variety of patterns to improve resolution of the apparatus 400. In certain embodiments two electrodes 302 inserted with the correct orientation may functionally provide nearly the same information as three electrodes 302. In one embodiment a single stimulation electrode 102 and an indifferent electrode (not shown) may be used to verify that a path for a surgical or other medical instrument is free of nerves 104.

Figure 6A:
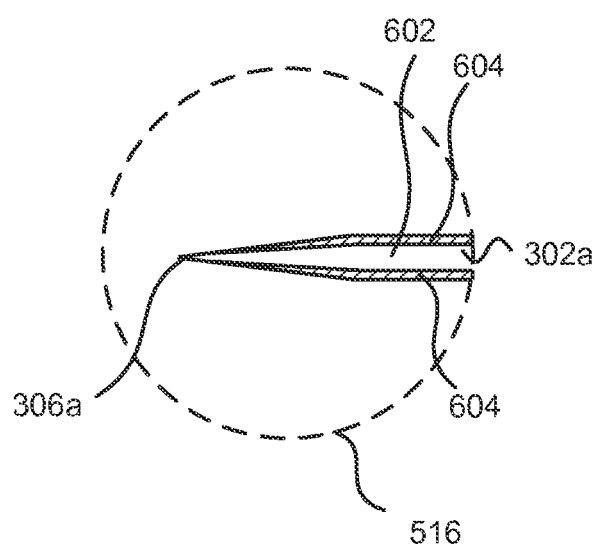
FIG. 6A depicts one embodiment of an enlarged cross sectional view of a tip area of a stimulation electrode.

FIG. 6A depicts one embodiment of an enlarged cross sectional view of the tip area 516 of stimulation electrode 302a of FIG. 5. In certain embodiments the stimulation electrodes 302 are smaller than a dilator or other instrument typically used in a surgical procedure.

In one embodiment the stimulation electrode 302 is made of a 28 gauge stainless steel or other electrically conductive and medically appropriate wire 602. In one embodiment the wire 602 may be covered with Teflon or other insulating material 604 which is ground back to bevel both the wire 602 and the insulating material 604. By beveling the wire 602 and the insulating material 604 the tip 306a is small while the shaft of the stimulation electrode 302a remains large enough to be substantially rigid. The small tip 306a of the stimulation electrode 302a reduces the chance of hitting the nerve 104 directly, and reduces the likelihood of injury to the nerve 104 if the stimulation electrode 302a touches the nerve 104.

Figure 6B:
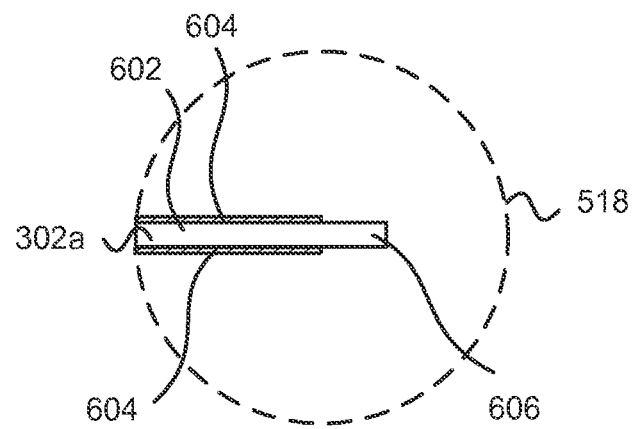
FIG. 6B depicts one embodiment of an enlarged cross sectional view of a lead coupling area of a stimulation electrode.

FIG. 6B depicts one embodiment of an enlarged cross sectional view of the lead coupling area 518 of stimulation electrode 302a of FIG. 5. In certain embodiments the Teflon or other insulating material 604 is ground hack or otherwise removed from the wire 602 leaving a coupling lead 606 for coupling the stimulation electrode 302a to the electrical source 403 or control module 401.

Each electrode 502 is individually insulated with Teflon or another insulating material 604 except for the tip 306 and the coupling lead 606. While the embodiments illustrated in FIGS. 6A and 6B are discussed with reference to stimulation electrode 302a, one of skill in the art will recognize that stimulation electrodes 302b and 302c may be substantially similar to stimulation electrode 302a.

Figure 7:
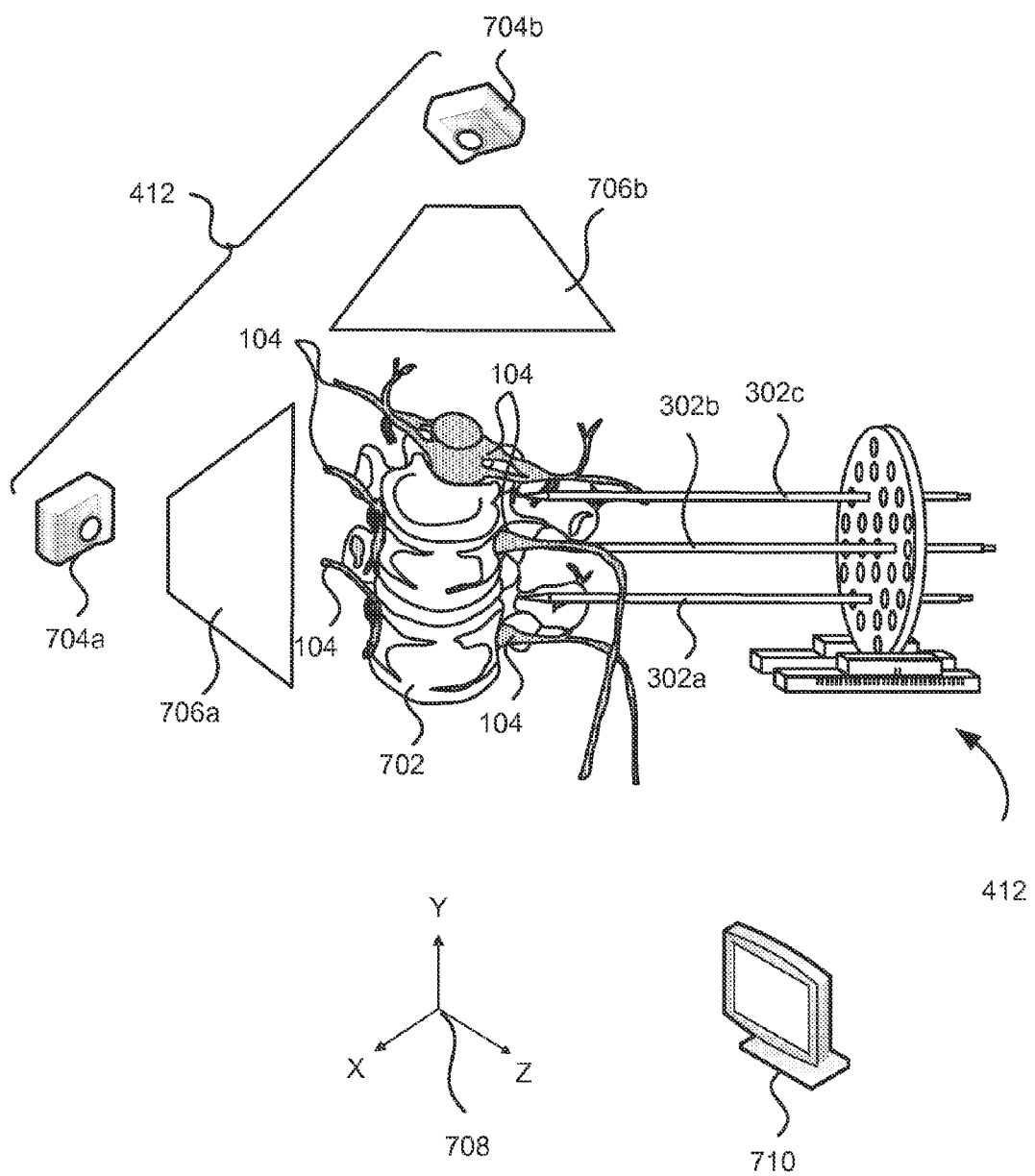
FIG. 7 depicts one embodiment of a portion of a patient's spinal column with the positioning module positioning three stimulation electrodes near fee patient's spinal column and an imaging module having two imaging devices.

FIG. 7 depicts one embodiment of a portion of a patient's spinal column 702 with the electrode positioning module 410 positioning three stimulation electrodes 302 near the patient's spinal column 702. FIG. 7 also illustrates one embodiment of the imaging module 414 having two imaging devices 704.

In certain embodiments each imaging device 704 captures an image 706 of a user's anatomy from a different angle. In one embodiment the images 706 are captured from at least two angles. In certain embodiments the angles are offset by ninety degrees such that the images 706 show both the x and y axis as well the z axis of a Cartesian coordinate system 708. The images 706 may then be combined to give a three-dimensional image of the user's anatomy to a physician or other operator. In the embodiment depicted in FIG. 7 the Cartesian coordinate system 703 is illustrated for clarity purposes only.

In certain embodiments the mapping module 408 uses distances calculated by the distance module 406 to map the location of a nerve 104. In the embodiment illustrated in FIG. 7 several nerves 104 are depicted. In certain embodiments the apparatus 400 may be used to map each of the nerves 104 in the manner described above.

The overlay module 418 overlays the map of the nerve(s) 104 on the image(s) 706 captured by the imaging device(s) 704. In one embodiment the stimulation electrodes 302 may be made of a material detectable by the imaging module 414 such that the stimulation electrodes 302 are shown in the images 706 captured by the imaging devices 704. In another embodiment the marking module 420 may position a marker (not shown) made of a material detectable by the imaging module 414 at or near the position of each stimulation electrode 302. In certain embodiments the overlay module 418 uses the stimulation electrodes 302 or the markers (not shown) as reference indicators to aid in positioning the map of the nerve 104 in an appropriate position on the images 706.

In certain embodiments a display unit 710 displays the images 706 of the patient's anatomy along with the overlaid map of the nerve 104 so that a physician or other user can avoid the nerve 104 in performing a medical procedure. In one embodiment each image 706 is displayed separately so that the physician or other user can determine the position of nerve 104 in three dimensions. In another embodiment the two images 706 may be combined and displayed on the display unit 710 using three dimensional rendering as is known in the art.

Figure 8:
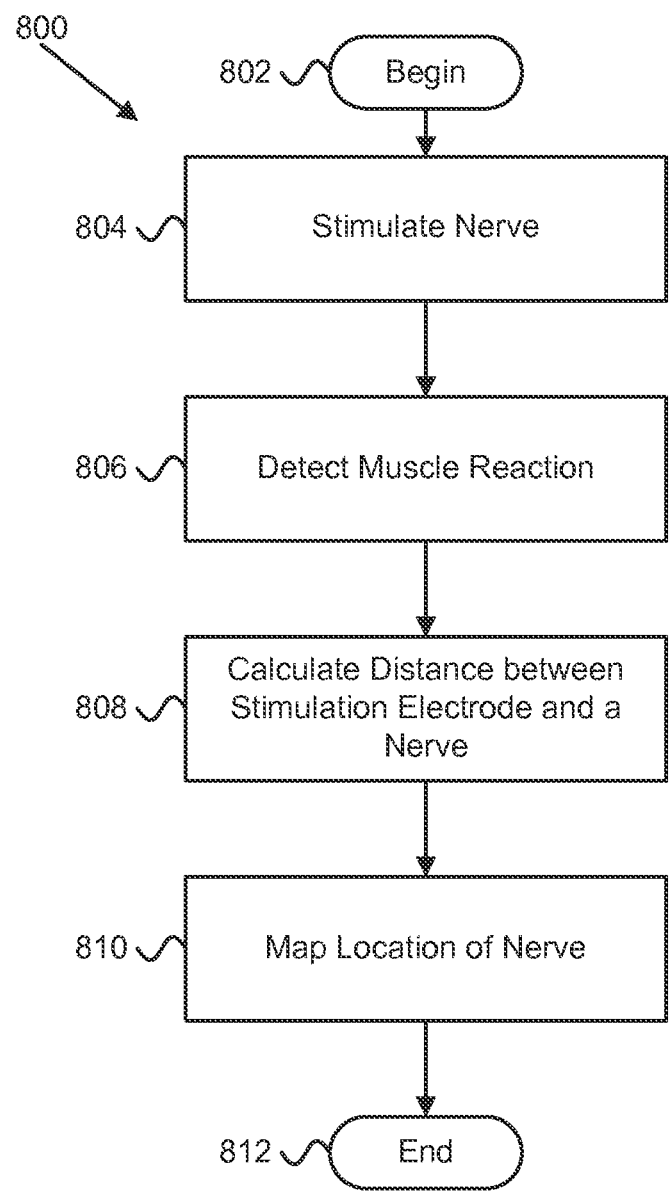
FIG. 8 depicts a schematic block diagram of one embodiment of a method for mapping the location of a nerve.

FIG. 8 is a schematic block diagram depicting one embodiment of a method 800 for mapping the location of a nerve 104 such as may be used with the apparatus 400 of FIG. 4. The method 800 starts 802 and a stimulation module 402 stimulates 804 a nerve with an electrical stimulation current from at least one stimulation electrode 102. In certain embodiments the nerve 104 is stimulated 804 by three stimulation electrodes such as stimulation electrodes 302. In such an embodiment the nerve 104 may be stimulated 804 by each stimulation electrode 302 independently, that is, in certain embodiments a first stimulation electrode 302a stimulates 804 the nerve 104 first, a second stimulation electrode 302b stimulates 804 the nerve 104 second and a third stimulation electrode 302c stimulates 804 the nerve 104 third.

In one embodiment each stimulation electrode 102 (or stimulation electrodes 302) may stimulate 804 the nerve with a current that is increased until a threshold muscle reaction is detected 806 by a stimulation detection module 404. In certain embodiments the muscle reaction results from the stimulation 804 of the nerve by the at least one stimulation electrode 102 (or stimulation electrodes 302).

In certain embodiments the muscle reaction is detected 806 by a electromyograph. In other embodiments the muscle reaction may be detected 806 by physical observation of the patient's anatomy or muscles.

A distance module 406 calculates 808 a distance between the at least one stimulation electrode 102 (or stimulation electrodes 302) and the nerve 104 using current information from the at least one stimulation electrode 102 (or stimulation electrodes 302) at a time of first detecting 806 the muscle reaction. In one embodiment the distance module 406 uses Coulomb's law to calculate 808 the distance between the at least one stimulation electrode 102 (or stimulation electrodes 302) and the nerve 104. In other embodiments the distance module 406 uses any formula that calculates 808 distance as function of a stimulation current required to invoke an electromyogram response in the muscle.

In certain embodiments a mapping module 408 maps 810 a location on the nerve 104 using at least two distance calculated 808 and position information of the at least one stimulation electrode 102 (or stimulation electrodes 302) for each of the at least two distances calculated 808. In one embodiment the mapping module 408 uses at least three distances calculated 808 to map 810 the location on the nerve. In either case, each of the distances calculated indicates a spherical locus of potential sites 108 (or spherical locus of potential sites 308) on the nerve 104 equidistant from a position of the at least one stimulation electrode 102 (or stimulation electrodes 302) when the at least one stimulation electrode 102 (or stimulation electrodes 302) stimulates 804 the nerve 104.

In embodiments where distances are calculated 808 to map 810 a location on the nerve 104, the location on the nerve 104 can be determined to lie somewhere on an intersection of the two of the spherical locus of potential sites which is a circle, such as the circle 214 created by the intersection of the two spherical locus of potential sites 208 as illustrated in FIG. 2 and discussed above. In certain embodiments pinpointing the location on a nerve 104 with an accuracy of circle 214 may be enough to perform certain medical procedures. In one embodiment a physician's or other professional's knowledge of a patient's anatomy may be used in combination with the method presented herein to pinpoint a location on the nerve 104 using only two distance calculations.

In other embodiments a medical procedure may call for greater accuracy. In such an embodiment three distances may calculated 803 to map 810 a location on the nerve 104. Where three distances are used to map 810 the location on the nerve 104 the location can be determined to be at one of two positions 316 identified by the intersection of three spherical locus of potential sites 308 as illustrated in FIG. 3 and discussed above. In a further embodiment more than three distances may be calculated 808 to map 810 the location on the nerve 104 with greater accuracy. Upon mapping 810 the location of the nerve, the method ends 812.

Figure 9:
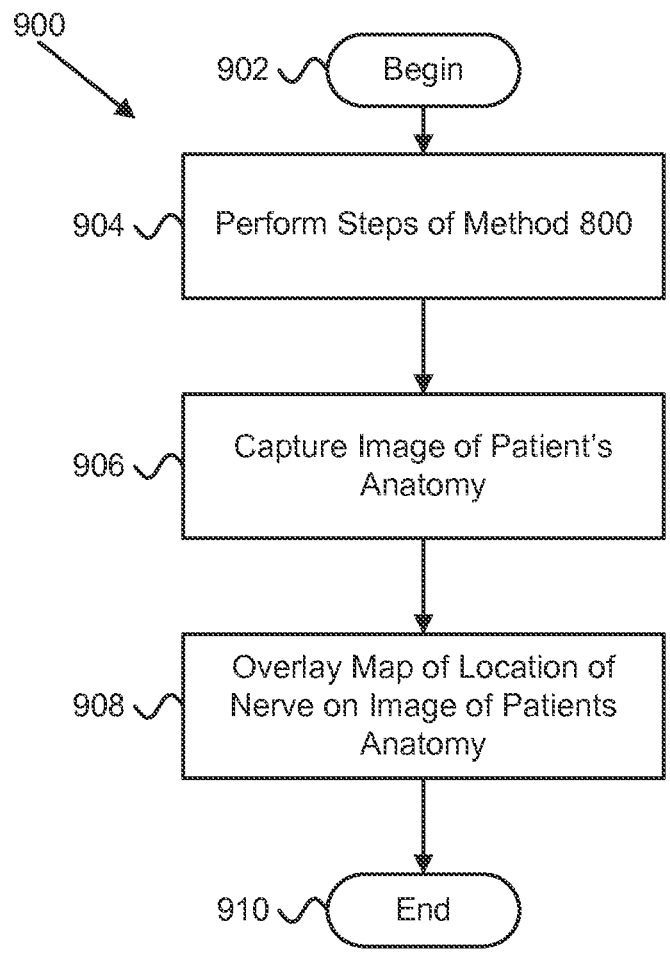
FIG. 9 is a schematic block diagram depleting another embodiment of a method for mapping the location of a nerve.

FIG. 9 is a schematic block diagram depicting one embodiment of a method 900 for mapping the location of a nerve 104. In certain embodiment the method 900 begins 902 and the steps of method 800 are performed 904. In certain embodiments the method 900 includes capturing 906 an image a patient's anatomy and overlaying 908 a map of the location on the nerve 104 on the image of the patient's anatomy and the method ends 910. In one embodiment the map of the location on the nerve 104 may be overlaid 906 on the image of the patient's anatomy in three dimensions such that the physician may determine the location of the position on the nerve 104 in three dimensions.

The present subject matter may be embodied in other specific forms without departing from its spirit or essential characteristics. The described embodiments are to be considered in all respects only as illustrative and not restrictive. The scope of the subject matter is, therefore, indicated by the appended claims rather than by the foregoing description. All changes which come within the meaning and range of equivalency of the claims are to be embraced within their scope.

What is claimed is:

1. An apparatus to map locations of nerves, the apparatus comprising circuitry configured to:
   stimulate a nerve with an electrical stimulation current from at least one stimulation electrode at a first area of a patient and a second area of the patient;
   detect a respective muscle reaction resulting from stimulation of the nerve by the at least one stimulation electrode at both the first area of the patient and the second area of the patient;
   determine, for the first area and the second area, a first spherical locus of potential sites of the nerve equidistant from a first position of the at least one stimulation electrode using a distance, calculated based on the detected muscle reaction, between the first position of the at least one stimulation electrode and the nerve;
   determine, for the first area and the second area, a second spherical locus of potential sites of the nerve equidistant from a second position of the at least one stimulation electrode using a distance, calculated based on the detected muscle reaction, between the second position of the at least one stimulation electrode and the nerve;
   map a first location on the nerve by determining a first intersection between the first spherical locus at the first area and the second spherical locus at the first area;
   map a second location on the nerve by determining a second intersection between the first spherical locus at the second area and the second spherical locus at the second area; and
   determine a route of the nerve as the nerve passes between the first location on the nerve and the second location on the nerve based on a determined curve between the first location on the nerve and the second location on the nerve.

2. The apparatus of claim 1, wherein the circuitry configured to detect the muscle reaction comprises an electromyography that detects an electrical potential generated by a muscle cell in response to stimulation of the nerve by the at least one stimulation electrode.

3. The apparatus of claim 1, wherein the at least one stimulation electrode comprises, at the first area, a first stimulation electrode, a second stimulation electrode, and a third stimulation electrode, the first stimulation electrode stimulating the nerve from the first position to calculate the first distance, the second stimulation electrode stimulating the nerve from the second position to calculate the second distance, the third stimulation electrode stimulating the nerve from a third position to calculate a third distance, and wherein the circuitry is further configured to map the first location of the nerve using the first distance, the second distance, and the third distance.

4. The apparatus of claim 3, wherein the circuitry is further configured to move the first stimulation electrode, the second stimulation electrode, and the third stimulation electrode to a new area, wherein at each new area of a stimulation electrode, the circuitry further determines one or more additional locations on the nerve.

5. The apparatus of claim 1, wherein the circuitry is further configured to position the at least one stimulation electrode in at least three positions.

6. The apparatus of claim 5, wherein the circuitry configured is further configured to move the at least one stimulation electrode to a new area to determine one or more additional locations on the nerve.

7. The apparatus of claim 1, wherein the circuitry is further configured to;
   capture an image of a patient's anatomy; and
   overlay a map of the first location on the nerve on the image of the patient's anatomy.

8. The apparatus of claim 7, wherein the circuitry is further configured to mark a position of the at least one stimulation electrode with a marker comprising a detectable material to position the map of the first location on the nerve on the image of the patient's anatomy.

9. The apparatus of claim 7, wherein the circuitry is further configured to capture a three dimensional image of the patient's anatomy and overlay the map of the first location on the nerve in three dimensions such that the first location on the nerve within the patient's anatomy is identified in three dimensions.

10. The apparatus of claim 7, wherein the circuitry comprises one or more of an imaging device selected from an x-ray device, a computerized axial tomography device, a magnetic resonance imaging device, and an ultrasound device.

11. An apparatus to map locations of nerves, the apparatus comprising:
at least one stimulation electrode that stimulates a nerve with an electrical stimulation current from an electrical source at a first area of a patient and a second area of the patient; and
circuitry configured to:
  detect a respective muscle reaction resulting from stimulation of the nerve by the at least one stimulation electrode at both the first area of the patient and the second area of the patient;
  determine, for the first area and the second area, a first spherical locus of potential sites of the nerve equidistant from a first position of the at least one stimulation electrode using a distance, calculated based on the detected muscle reaction, between the first position of the at least one stimulation electrode and the nerve;
  position the at least one stimulation electrode at a second position to determine, for the first area and the second area, a second spherical locus of potential sites of the nerve equidistant from the second position using a distance, calculated based on the detected muscle reaction, between the second position of the at least one stimulation electrode and the nerve;
  map a first location on the nerve by determining a first intersection between the first spherical locus at the first area and the second spherical locus at the first area;
  map a second location on the nerve by determining a second intersection between the first spherical locus at the second area and the second spherical locus at the second area; and
  determine a route of the nerve as the nerve passes between the first location on the nerve and the second location on the nerve based on a determined curve between the first location on the nerve and the second location on the nerve.

12. The apparatus of claim 11, wherein the circuitry is further configured to:
capture an image of a patient's anatomy; and
overlay a map of the first location on the nerve on the image of the patient's anatomy.

13. A method for mapping locations of nerves, the method comprising:
stimulating, using control circuitry, a nerve with a stimulation current from at least one stimulation electrode at a first area of a patient and a second area of the patient;
detecting, using the control circuitry, a respective muscle reaction resulting from stimulation of the nerve by the at least one stimulation electrode at both the first area of the patient and the second area of the patient;
calculating, using the control circuitry, for the first area and the second area, a first distance between the at least one stimulation electrode at a first position and the nerve using current information from the at least one stimulation electrode at a time of first detecting the muscle reaction to determine a first spherical locus of potential sites of the nerve equidistant from the first position of the at least one stimulation electrode; and
calculating, using the control circuitry, for the first area and the second area, a second distance between the at least one stimulation electrode at a second position and the nerve using current information from the at least one stimulation electrode at the time of first detecting the muscle reaction to determine a second spherical locus of potential sites of the nerve equidistant from the second position of the at least one stimulation electrode;
mapping, using the control circuitry, a first location on the nerve by determining a first intersection between the first spherical locus at the first area and the second spherical locus at the first area;
mapping, using the control circuitry, a second location on the nerve by determining a second intersection between the first spherical locus at the second area and the second spherical locus at the second area; and
determining, using the control circuitry, a route of the nerve as the nerve passes between the first location on the nerve and the second location on the nerve based on a determined curve between the first location on the nerve and the second location on the nerve.

14. The method of claim 13, further comprising:
capturing, using the control circuitry, an image of a patient's anatomy; and
overlaying, using the control circuitry, a map of the first location on the nerve on the image of the patient's anatomy.

* * * * *